United States Patent [19]

Cohen

[11] Patent Number: 4,730,622
[45] Date of Patent: * Mar. 15, 1988

[54] PRESSURE AND OXYGEN SATURATION CATHETER

[75] Inventor: Donald M. Cohen, Miami, Fla.

[73] Assignee: Cordis Corporation, Dade, Fla.

[*] Notice: The portion of the term of this patent subsequent to Sep. 8, 2004 has been disclaimed.

[21] Appl. No.: 895,898

[22] Filed: Aug. 12, 1986

Related U.S. Application Data

[63] Continuation-in-part of Ser. No. 881,476, Jul. 1, 1986, Pat. No. 4,703,757, which is a continuation of Ser. No. 671,913, Sep. 16, 1984, abandoned.

[51] Int. Cl.[4] .............................................. A61B 5/02
[52] U.S. Cl. .................................. 128/667; 128/675; 128/748; 73/705; 250/231 P
[58] Field of Search ............... 128/748, 667, 673, 675, 128/634; 73/705; 350/96.32, 96.33; 250/231 P

[56] References Cited

U.S. PATENT DOCUMENTS

| | | | |
|---|---|---|---|
| 3,051,003 | 8/1962 | Witt | 73/705 |
| 4,201,222 | 5/1980 | Haase | 128/634 |
| 4,487,206 | 12/1984 | Aagand | 128/634 |
| 4,543,961 | 10/1985 | Brown | 128/748 X |

Primary Examiner—William E. Kamm
Assistant Examiner—John C. Hanley
Attorney, Agent, or Firm—Tarolli, Sundheim & Covell

[57] ABSTRACT

Apparatus is provided for simultaneously measuring the oxygen content in blood as well as blood pressure at one or more sites within a body cavity or blood vessel. An elongated optical fiber is located within a catheter capable of being inserted into a body cavity. The distal end of the catheter contains a filter covering an end hole so that light may be transmitted through the filter at wavelengths in the red and infrared region while reflecting light of other wavelengths. This permits measurement of the oxygen content of blood. The optical fiber is coaxially surrounded by cladding means essentially throughout its length and is uncladded for at least a portion of its length near the distal end thereof. The catheter carries a pressure transducer associated with the uncladded core portion. The pressure transducer includes a flexible transducer member having an irregular surface facing the uncladded core portion for making surface area contact therewith so that the contacting surface area varies with applied pressure acting transversely of the catheter.

15 Claims, 26 Drawing Figures

PRESSURE AND OXYGEN SATURATION CATHETER

RELATED APPLICATION

This is a continuation-in-part of my previously filed U.S. Application Ser. No. 881,476 filed on July 1, 1986, now U.S. Pat. No. 4,703,757, and which in turn was a continuation of application Ser. No. 671,913 filed on Sept. 16, 1984, now abandoned.

BACKGROUND OF THE INVENTION

This invention relates to a catheter system for measuring blood pressure while simultaneously measuring the degree of oxygen saturation in blood. The invention is described in conjunction with measuring oxygen saturation as well as blood pressure within the cardiovascular system, although these two parameters may be measured in other systems of the body.

It is known in the prior art to provide an optically based catheter system for measuring the degree of oxygen saturation in blood of a living body while simultaneously measuring blood pressure at a site of interest. Such systems are known, for example, in the U.S. Pat. Nos. to Takayama, 3,822,695 and Mori, 3,814,081. In such systems, the two parameters, oxygen and blood pressure, are measured simultaneously employing an elongated catheter containing a bundle of optical fibers. These catheters are provided with an end hole at the distal end with the end hole being covered with a diaphragm. The diaphragm is transparent to light passing through the optical fibers in the red and infrared regions, but reflects light at shorter wavelengths. The oxygen content of blood is determined in such systems by comparing the absorption of light in the infrared region to absorption of light in the red region. Thus, carbohemoglobin and oxyhemoglobin in the blood are different in the light absorption spectrum. Both have like absorption rates for light in the infrared region, but carbohemoglobin has a much larger absorption rate for light in the red region. The percentage content of oxygen contained in the blood, that is, the ratio of oxyhemoglobin to carbohemoglobin is obtained in such systems by transmitting light in both the red and infrared regions into blood and then detecting light reflected from the blood and determining therefrom the ratio of the amount of reflected light in the two regions.

The systems described in the aforesaid patents measure the blood pressure at the site of interest with the diaphragm covered end hole. The diaphragm reflects the shorter wavelength light back into the optical fibers for transmission to an externally located meter. Since the catheter is inserted into the bloodstream of a patient, the blood pressure deflects the diaphragm, causing modulation of the light intensity so that the meter provides an indication of blood pressure.

Such catheters employing diaphragm covered end holes actually measure total pressure rather than the desired measurand; mainly, static pressure. By aligning the end hole of a catheter with the direction of blood flow, kinetic energy terms are introduced. If the catheter end hole is directed upstream, a kinetic term will be added to the pressure. If the end hole is facing downstream, the kinetic term will be subtracted from the pressure. The magnitude of the error will vary with the velocity and density of the fluid. This error will vary during the course of a cardiac cycle and will distort the shape and magnitude of a pressure wave. In the pulmonary artery, the kinetic pressure may be on the order of 10% of total pressure at rest and 50% of total pressure at a cardiac output equal to three times that at rest. The importance of the kinetic pressure error is particularly great in stenotic areas where velocities are high.

The catheters discussed above are also limited in their application to measuring pressure at a single site at a time. If pressure readings are required at different sites, then the readings must be taken at different times and the catheter must be moved so the transducer at the distal end is moved from site to site.

It is known in the prior art to provide a catheter capable of performing intravascular pressure measurements in more than one site with the readings being taken simultaneously. One such device known in the prior art is disclosed in the U.S. Pat. No. 4,543,961, to D. C. Brown, assigned to the same assignee as the present invention. In Brown, there is provided an elongated catheter having a plurality of optical fibers aligned end-to-end in the lumen of the catheter. A plurality of pressure transducers are provided along the length of the catheter with each being associated with the spacing between two aligned optical fibers. The pressure transducer includes a filter-mirror which is movable between the adjacent ends of two spaced apart fibers, the movement being in response to pressure acting against the catheter. Light is directed into the proximal end of the catheter and is transmitted by the optical fibers. At each pressure transducer, light at one wavelength only will be modulated in accordance with pressure. All other light will remain nearly unchanged. Consequently, at the proximal end, the reflected light of three different colors may be individually examined to determine the pressure exerted at each of the three sites under examination.

The multiple site pressure transducer structure in Brown serves to provide measurements of but a single blood parameter; namely, blood pressure. There is no teaching of measuring other blood parameters, such as the oxygen saturation in blood. Moreover, Brown's construction employs a plurality of optical fibers aligned end-to-end within the lumen of an elongated catheter. This results in difficulty of construction, since a typical catheter may have a diameter on the order of 0.06 inches and the optical fiber carried therein may be on the order of 400 micra. Placing a plurality of such fibers in end-to-end alignment along with associated filter-mirrors within such a catheter presents substantial difficulty in manufacture.

SUMMARY OF THE INVENTION

It is a primary object of the present invention to provide an improved catheter for use in measuring a plurality of blood parameters, including pressure and oxygen.

It is a still further object of the present invention to provide such a catheter having an improved optical fiber pressure transducer employing side port measuring of static pressure as opposed to end hole monitoring of total pressure.

It is a still further object of the present invention to provide such an improved catheter which permits measurement of oxygen saturation in blood while simultaneously obtaining measurement of static blood pressure at one or more sites of interest.

In accordance with the present invention, the foregoing and other objectives are achieved in a fiber optic based catheter system for measuring blood pressure at one or more locations while simultaneously measuring oxygen saturation in blood. The apparatus includes an elongated tubular catheter having a proximal end and a distal end with the latter adapted to be inserted into a passageway within a body cavity containing blood. A single elongated optical fiber is carried within the catheter and extends throughout the length thereof for receiving light at the proximal end of the catheter and transmitting it to the distal end thereof. The distal end of the catheter is provided with an end hole which is covered by a filter which passes light in the red and infrared region, but reflects light of shorter wavelengths. The filter is positioned forwardly of the distal end of the optical fiber to receive light therefrom. The filter reflects light of shorter wavelength back into the distal end of the optical fiber so that the reflected light is transmitted back to the proximal end of the catheter. The longer wavelength light, i.e., that in the red and infrared region, is passed by the filter and reflected differently by the blood in dependence upon oxygen saturation. The differently reflected light is passed back through the filter to the optical fiber for passage to the proximal end of the catheter. A detector may be located near the proximal end of the catheter and respond to the returned light in the red and infrared region to provide an indication as to the oxygen saturation in the blood. The catheter carries one or more pressure transducers which operate on the optical fiber for measuring pressure acting transversely thereof. The optical fiber is coaxially surrounded by cladding means essentially throughout its length and is uncladded for at least one portion of its length proximate to the distal end thereof. The pressure transducer is located adjacent the uncladded portion and includes a flexible transducer member having an irregular surface facing the uncladded core portion for making surface area contact therewith such that the contacting surface area varies with pressure applied to the transducer member acting transversely of the uncladded core portion. The transducer member is constructed of material exhibiting a greater index of refraction than the cladding so that the intensity of light passing through the core proximate to the transducer member is modulated in its intensity as a function of the transversely acting pressure.

In accordance with another aspect of the present invention, the catheter carries a plurality of pressure transducers, each is operating on an uncladded portion of the length of the core.

In accordance with a still further aspect of the present invention, the plurality of pressure transducers each include light wavelength dependent means for modulating light at a particular wavelength different from that at the other of the transducers.

BRIEF DESCRIPTION OF THE DRAWINGS

The foregoing and other objects and advantages of the present invention will become more apparent from a consideration of the following description as taken in conjunction with the accompanying drawings, wherein.

DETAILED DESCRIPTION OF PREFERRED EMBODIMENTS

Figure 1:
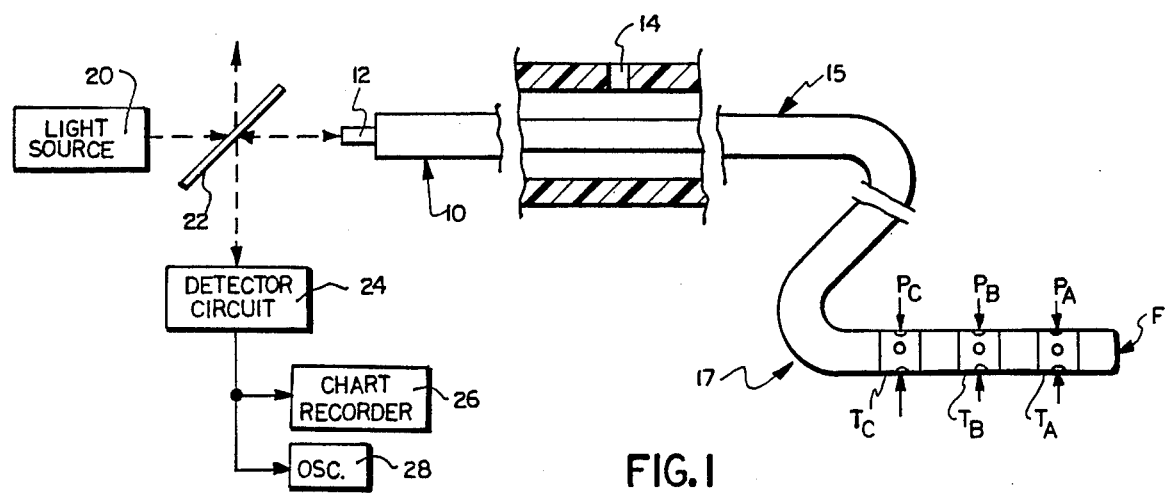
FIG. 1 is a schematic illustration of a multi-site pressure measuring catheter in conjunction with one application of this invention.

Reference is now made to the drawings wherein the showings are for purposes of illustrating preferred embodiments only, and not for limiting same. FIG. 1 illustrates an application of the invention as applied to simultaneous measurement of blood pressure as well as the degree of oxygen saturation of blood within a patient's cardiovascular system. This includes an elongated single lumen catheter 10 containing an optical fiber 12 which extends throughout the length of the catheter. At its distal end, the catheter carries a filter F employed for use in measuring the degree of oxygen saturation in the blood. In addition, the catheter carries three blood pressure transducers $T_A$, $T_B$, and $T_C$ for simultaneously measuring the blood pressure within the cardiovascular system at three different sites, such as sites A, B and C. The spacing between the pressure transducers may be varried as desired and, for example, the transducer $T_A$ may be located adjacent the distal end of the catheter with transducers $T_B$ and $T_C$ spaced therefrom toward the proximal end. It is contemplated, for example, that these transducers may be used for simultaneously recording of pulmonary wedge pressure, right ventricular pressure, and atrial pressure. In such case, the transducers will be spaced approximately 10 centimeters apart.

As will be described in greater detail with respect to the three specific embodiments disclosed herein, filter F at the distal end of the catheter is chosen to transmit light in the red and infrared regions and to reflect light of shorter wavelengths. In this context, it has been determined that there is a large difference in light reflectance between oxygenated and unoxygenated blood with light having a wavelength on the order of 805 nanometers. However, the reflectance is equal for both oxygenated and unoxygenated blood for light having a wavelength on the order of 930 nanometers Consequently, the ratio of light reflected from blood at wavelengths of 805 nanometers and 930 nanometers provides an indication of the degree of oxygen saturation of blood. For this reason, then, the filter F is chosen to transmit light above approximately 750 nanometers, while reflecting light below that level. The light source is chosen to emit a broad band of light, including light in the range from approximately 750 nanometers through 950 nanometers for oximetry and light in another waveband (e.g., 350–700 nm) for pressure sensing. This light passes through the optical fiber 12 and then to the distal end thereof, at which the longer wavelength light, i.e., above 750 nanometers is transmitted through the filter F into the bloodstream. There, light is reflected differently at 805 nanometers and at 930 nanometers, as discussed above. This light reflected from the blood is redirected back into the optical fiber to the proximal end thereof. The detector circuit 24 in addition to detecting blood pressure, also includes detector circuitry for determining the ratio of light reflected at 805 nanometers to that reflected at 930 nanometers. This provides an indication of the oxygen saturation of blood and this information may then be displayed as with the use of a conventional chart recorder 26, or displayed as with an oscilloscope 28.

The catheter 10 preferably takes the form of a torque controlled catheter, such as that constructed in accordance with the U.S. Pat. No. 3,585,707, R. C. Stevens, assigned to the same assignee as the present invention and disclosure of which patent is herein incorporated by reference. Briefly, as described in that patent, the catheter is an intravascular catheter having an elongated body portion 15 and a tip portion 17 at the distal end of the catheter. The body portion 15 is reinforced so that it may be twisted at its proximal end to impart a twisting motion throughout its length. This body portion is constructed to have high longitudinal flexibility and high torsional control without being elastic. Moreover, the body portion includes tubing made up of an inner plastic tubular core covered by a braided wire intermediate sheath and an outer plastic covering which penetrates through the interstices in the braiding of the sheath and closely overlies the tubular core.

The tip portion 17 is designed to direct the catheter during insertion into a selected body vessel and is preferably formed with a tapered end as a pair of curves including a relatively sharp curve on the order of 45° just before the distal end thereof and a less sharp curve a short distance proximally thereof. The tip portion 17 does not employ a braided sheath and it is preferably more flexible than the body portion.

As will be described in greater detail hereinafter with respect to each embodiment of the invention, each of the transducers serves to measure pressure acting in a direction transversely of the long axis of the optical fiber. For this purpose, each transducer is provided with an array of side ports spaced equidistant apart circumferentially about the catheter with each side port being covered with an elastic membrane which may, for example, take the form of silastic. Each membrane covers a transducer member constructed of flexible material having an index of refraction greater than that of the cladding and serves to make surface area contact with an uncladded core portion of the optical fiber. The contacting surface area will vary with pressure applied to the transducer acting transversely of the optical axis of the optical fiber. As the pressure increases, more light will be refracted and absorbed by the transducer member. Consequently, any light entering the proximal end of the optical fiber 12 will be modulated in each of the pressure transducers in dependence upon the magnitude of the pressures applied at the transducer sites. A mirror surface is provided at the distal tip of the optical fiber so that the light reflected therefrom is again modulated at the transducers as the light returns to the proximal end of the optical fiber. To assist in measuring pressure relative to atmospheric pressure, the catheter is vented, as with an aperture 14 in the wall of the catheter at a location near the proximal end where it is exterior to the patient.

In general, it is contemplated that for each embodiment herein, there will be provided a suitable light source 20 which transmits light into the proximal end of the optical fiber 12 so that the light may be modulated in dependence upon the pressure applied to each of the transducers $T_A$, $T_B$ and $T_C$. The input light may first pass through a beam splitter 22 which passes a portion of the light into the proximal end of the optical fiber 12 and directs the remaining light in an upward direction. Light that has been modulated and reflected from the distal end of the catheter is returned to the proximal end of the optical fiber 12 and is passed to the beam splitter 22 and a portion of this modulated light is then directed downwardly to an optical detector circuit 24. As will be described with respect to each embodiment, the detector circuitry operates to determine from the modulated light the values of the pressures $P_A$, $P_B$ and $P_C$ acting at the monitored sites A, B and C. This information may then be displayed as with the use of a conventional chart recorder 26 and/or displayed as with an oscilloscope 28. Having now provided a general description of one application of the invention, attention is directed to the specific description of each of the embodiments herein as presented below.

Figure 2:
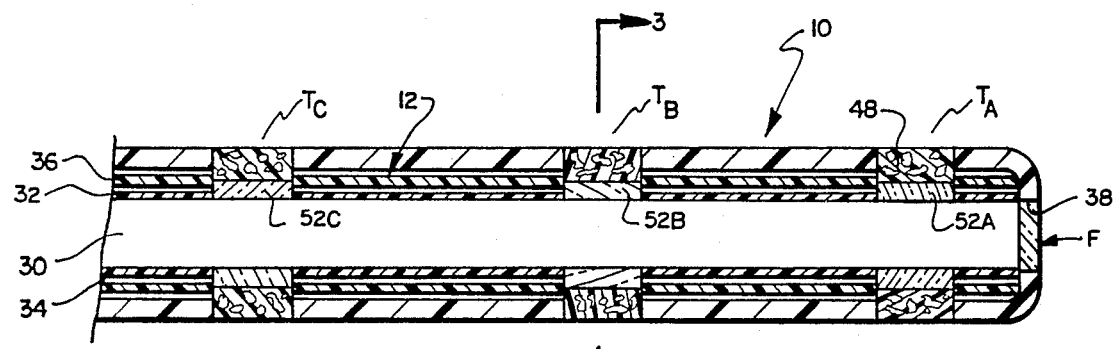
FIG. 2 is an enlarged sectional view of the distal end of the catheter in accordance with one embodiment of the invention.

Reference is now made to FIG. 2 which presents an enlarged sectional view of the distal end of catheter 10 and showing pressure transducers $T_A$, $T_B$ and $T_C$. As seen, the catheter 10 is a single lumen, thin wall catheter, such as that provided by Cordis Corporation, and known as Cordis FR5 Thin Wall Catheter. This catheter may have a diameter on the order of 0.066 inches and is constructed of plastic material, such as polyurethane. The optical fiber 12 carried within the single lumen of the catheter preferably takes the form of a cladded multimode optical fiber. This fiber has a core 30 of a fluoropolymer of a diameter on the order of 400 micra. The core 30 is covered throughout essentially all of its length with cladding 32 constructed of an acrylic material having a thickness on the order of 16 micra. Surrounding the cladding 32 are Kevlar reinforcing strands 34 for purposes of strengthening the optical fiber 30. The Kevlar strands 34 are, in turn, covered with a layer of black Hytrel 36. Optical fibers, such as fiber 30, are commercially available. Light passing through the optical fiber 30 of wavelength greater than 750 nanometers is passed by filter F suitably mounted, as by bonding, to an end hole 38 at the distal end of the catheter. Light of shorter wavelength is reflected by the filter.

Figure 3:
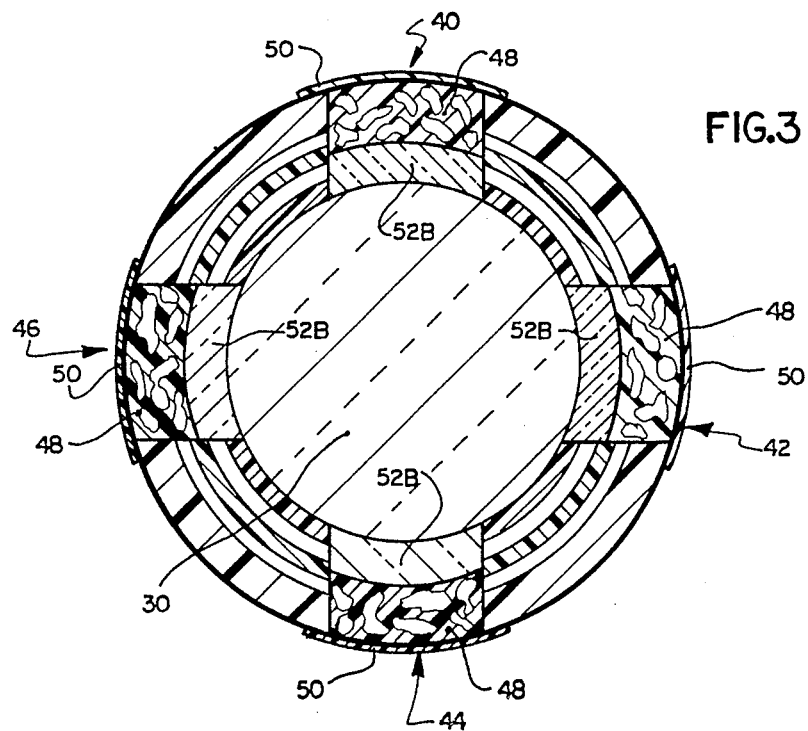
FIG. 3 is an enlarged sectional view taken along line 3—3 looking in the direction of the arrows of FIG. 2.

At the locations for each of the pressure transducers $T_A$, $T_B$ and $T_C$, the cladding is removed. At each location there are provided four side ports 40, 42, 44, and 46 spaced in an annular array equidistant from each other, as is best shown in FIG. 3, which is a cross sectional view taken along line 3—3 looking in the direction of the arrows in FIG. 2. On each of the side ports, the cladding 32 and strands 34 and coating 36 are removed and replaced with a sponge-like transducer insert 48. The outer surface of each insert may, in turn, be coated with a protective membrane 50 which may be of a latex material and may be formed by applying viscous liquid of latex over the insert filled side port in adjacent exterior surface areas of the catheter and then air drying it. The membrane, while covering the insert, will adhere and form a seal with the outer surface of the catheter, but will not adhere to the sponge-like material forming the transducer inserts.

In the embodiment shown in FIGS. 2 and 3, the inner surface of each transducer insert faces a portion of the uncladded surface of the optical core 30. Intermediate the insert and the uncladded core 30, there is provided an optical coating defining a filter. These filters are illustrated and identified as filters 52A, 52B and 52C.

The filters 52A, 52B and 52C are standard coatings with each filter having a different functional relationship between index of refraction and wavelength. Thus, these filters are so chosen that each will partially refract a different waveband and reflect all other wavebands. This will be discussed in greater detail hereinafter.

In the construction of the embodiment as shown in FIG. 2, the cladding is removed at the locations for transducers $T_A$, $T_B$ and $T_C$. This may be accomplished in a controlled manner, as with the use of a solvent, such as tetrahydrofuran, so that the removal takes place only at desired locations. The transducer inserts 48 are constructed of a sponge-like material, such as polyurethane foam. This may take the form of hypol foamable hydrophilic polyurethane polymer which may be obtained from the Organic Chemicals Division of the W. R. Grace & Company. This is a porous material and includes interconnecting pores. The insert may be held in place by an interference fit.

Figure 4:
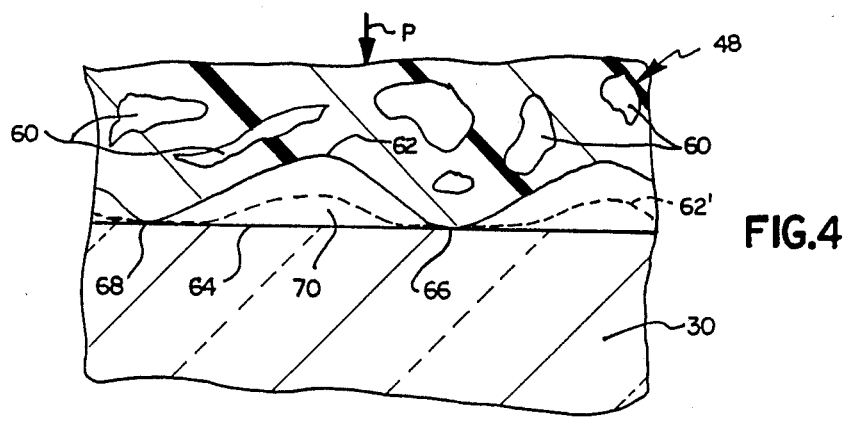
FIG. 4 is an enlarged view showing a portion of a transducer member in surface engagement with an uncladded core and used for purposes of explanation herein.

Reference is now made to FIG. 4 which is an enlarged sectional view showing a portion of the length of the uncladded optical fiber core 30 in engagement with a transducer insert 48. The transducer insert is made of a sponge-like material and has interconnecting pores 60. The interior surface 62 of the transducer insert is irregular in shape and makes intermittent surface contact with the surface 64 of the uncladded core 30, such as at locations 66 and 68 separated by an air pocket 70. The air pockets 70 are vented to the atmosphere by way of pores 60 and the annular space surrounding the cladded core within the lumen of the catheter 10 and which leads to the aperture 14 located near the proximal end of the catheter. This, then, provides the basis for a pressure differential with exterior applied pressure. As the pressure P increases, the interior surface 62 of the insert will move toward the uncladded surface 64, as indicated by the dotted lines 62', so as to increase the surface area contact with the uncladded surface 64. Likewise, as the pressure is removed, the sponge-like material, being resilient, will return to that as indicated by the solid line 62 and make less surface area contact with the uncladded surface 64. Pressure less than atmospheric will cause the surface 62 to move radially away from the core, thus reducing contact area. These variations in surface area contact between the transducer insert 48 and the uncladded surface of the optical fiber core with variations in pressure modulate the intensity of light traveling through the optical fiber. At this point, it is to be noted that the index of refraction n is different for the various materials employed. Thus, the index of refraction n for the fiber core 30 is on the order of 1.5 and for the surrounding air within the air pockets 60 and in the lumen, as vented to the atmosphere, is on the order of 1.0. The cladding 32 exhibits an index of refraction slightly less than that of core 30. However, light to be transmitted through filters 52 and be absorbed or refracted by the sponge inserts 48, the filters 52 must have an index of refraction greater than that of cladding 32 and, in turn, the inserts 48 must have an index of refraction greater than that of the filters so as to refract light that is passed by the filters.

Figure 5A:
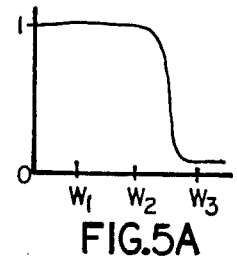
FIGS. 5A, 5B and 5C are graphical waveforms illustrating reflectivity versus wavelength useful in the description of the embodiment shown in FIGS. 2 and 3.
Figure 5B:
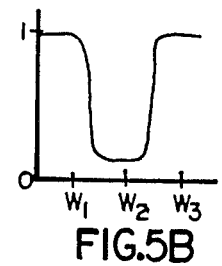
Figure 5C:
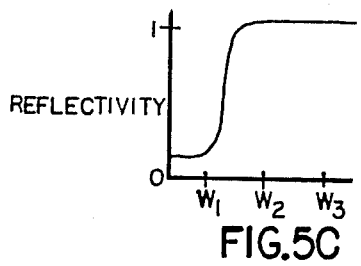
Figure 6A:
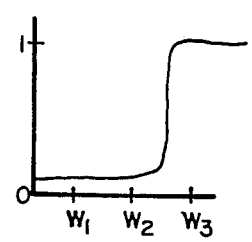
FIGS. 6A-6C are graphical waveforms illustrating light transmission as a function of wavelength and which is useful in the description of the embodiment of FIGS. 2 and 3.
Figure 6B:
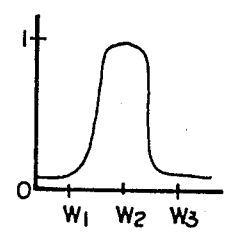
Figure 6C:
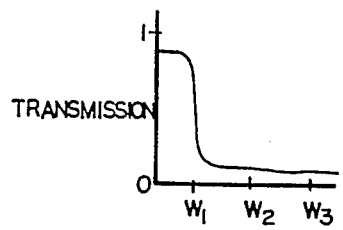

Each of the filters 52A, 52B and 52C pass light within a particular waveband and reflect the remaining light. Thus, for example, filter 52A reflects light within a waveband containing wavelengths $W_1$ and $W_2$ while passing light within a waveband containing light of wavelength $W_3$. This is illustrated in FIGS. 5A and 6A. Similarly, filter 52B passes light only within a waveband containing light in wavelength $W_2$, but reflects all remaining light, and this is illustrated in FIGS. 5B and 6B. Also, filter 52C passes light in a waveband containing wavelength $W_1$ while reflecting all remaining light, and this is illustrated in FIGS. 5C and 6C.

In this embodiment, the light source emits a broad band of light. A filament lamp or an arc lamp or other wide band light source may be employed as the light source 20. This light is passed by a beam splitter 22 and focused, as with a lens 74, into the proximal end of the optical fiber 12. The light that travels through the core 30 and which strikes the core-air interface (see FIG. 4) will be totally internally reflected. However, the light that strikes the core-sponge interface will be partially refracted and partially reflected. The amount of light that is refracted and thereby absorbed will be a function of the surface contact area. Thus, light that is traveling from the proximal end to the distal end of the catheter will pass through the transducer area and a portion of the light will be refracted in dependence upon the pressure P. The light that is internally reflected will be reflected back by the filter F at the distal end of the optical fiber. This reflected back light will also be attenuated as it passes the transducer area as it travels back toward the proximal end of the catheter. The intensity of light returning at the proximal end of the catheter will vary inversely with the pressure applied to the transducers.

At transducer $T_A$, only light that has been passed by filter 52A will be refracted and, hence, attenuated by the transducer insert 48. This light will be at wavelength $W_3$ and the remaining light is reflected by the filter 52A. Consequently, it is the light which exits from the proximal end of the optical fiber 12 at wavelength $W_3$ that includes the intelligence representing the pressure applied at transducer $T_A$.

In similar fashion, it is only the light exiting from the proximal end of the optical fiber at wavelength $W_2$ that includes the intelligence relative to the pressure applied at the transducer $T_B$. Also, it is only the light exiting from the proximal end of the optical fiber at wavelength $W_1$ that includes the intelligence as to the pressure at the transducer $T_C$.

Figure 7:
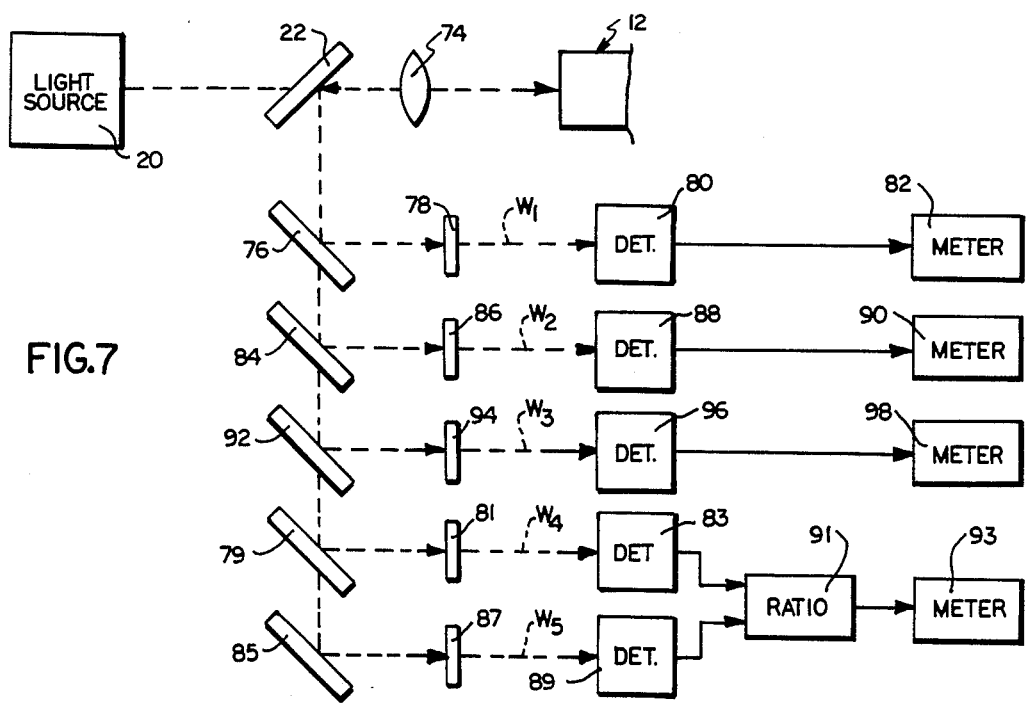
FIG. 7 is a schematic-block diagram illustration of the optical system as well as the electronic detecting circuitry employed in the embodiment of FIGS. 2 and 3.

Referring now to FIG. 7, it is seen that as the light exits from the proximal end of the optical fiber 12, it is applied by way of lens 74 to the beam splitter 22 and a portion is then directed in a downward direction. A first beam splitter 76 intercepts this light and directs a portion of it through a filter 78 that passes only light at wavelength $W_1$. This is detected by optical-electrical detector 80, which converts intelligence into an electric signal to drive a suitable meter 82 to provide an output indicative of the pressure at the transducer $T_C$. As the pressure at transducer $T_C$ increases, there will be a reduction in the amount of light returned to the proximal end at wavelength $W_1$. This is detected by detector 80 and displayed as with meter 82.

In a similar fashion, the light that is passed by the beam splitter 76 strikes a second beam splitter 84 and light reflected therefrom is passed through a filter 86 which passes light only at wavelength $W_2$. Detector 88 converts this information into an electrical signal which is supplied to a suitable meter 90. This circuitry provides an output indication representative of the pressure at transducer $T_B$. Also, light passing through the beam splitter 84 will strike an additional beam splitter 92 causing light reflected therefrom to be applied to a filter 94 which passes only light at wavelength $W_3$. This is detected by a suitable detector 96 which supplies an electrical signal to meter 98 for displaying an output signal representative of the pressure applied at transducer $T_A$.

The light from the light source 20 in FIG. 7 includes light in the red and infrared light regions, i.e., from at least 800 nanometers through 950 nanometers. This longer wavelength light through the filter F at the distal end of the catheter and is reflected by blood back into the catheter. As previously discussed, two peak wavelengths are of importance, namely, 805 nanometers and 930 namometers. The first may be considered as wavelength $W_4$ and the second as wavelength $W_5$.

Referring now to FIG. 7, light exiting from the proximal end of the optical fiber 12 is reflected by splitter 22 and a portion of the light passes through beam splitters 76, 84 and 92. Light passing through beam splitter 92 strikes another beam splitter 79 and a portion of the light is directed to a filter 81. This filter is selected to pass only light at wavelength $W_4$ and this is passed to a detector 83 which converts the optical intelligence into an electrical signal having a magnitude representative of the magnitude of light at wavelength $W_4$. This electrical signal is applied as one input to a ratio circuit 91.

In a similar fashion, light passing through splitter 79 strikes a mirror 85 and the reflected light is directed to a filter 87. This filter passes only light at wavelength $W_5$ and this is passed to a detector 89 that converts the optical intelligence into an electrical signal having a magnitude representative of the amount of light at this wavelength. This electrical signal is supplied as a second input to the ratio circuit 91. This ratio circuit provides an output signal corresponding to the ratio of light intensity at wavelength $W_4$ to that at $W_5$ and this is supplied to a meter 93 for providing a suitable output indication and which, in turn, provides an indication of the percentage of oxygen saturation of the blood.

Reference is now made to a second embodiment of the invention which is illustrated in FIGS. 8, 9, 10, 11 and 12. This embodiment is quite similar to that described thus far and, consequently, like components are identified with like character references and only the differences over the previous embodiment will be described in detail herein.

In this embodiment, no filters are employed. Instead, each of the transducer inserts 48A', 48B' and 48C' is doped with a different fluorescent dye. Each insert is covered on its exterior surface with a membrane, such as membranes 50 constructed in the same manner as that discussed hereinbefore with respect to membranes 50 in FIGS. 2 and 3. The fluorescent dye doped transducer inserts have been doped such that each fluoresces in a different waveband.

Figure 10C:
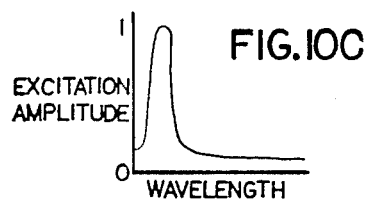
FIGS. 10A-10C are graphical waveforms illustrating excitation amplitude with respect to wavelength and is useful in describing the embodiment of FIGS. 8 and 9.
Figure 10B:
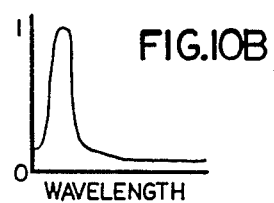
Figure 10A:
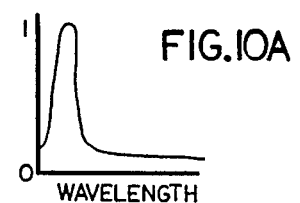
Figure 11C:
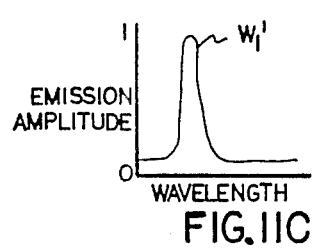
FIGS. 11A-11C are waveforms of emission amplitude versus wavelength and which is useful in describing the embodiments of FIGS. 8 and 9.
Figure 11B:
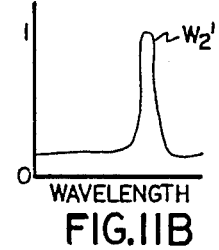
Figure 11A:
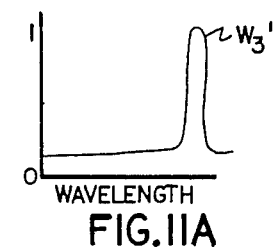
Figure 12:
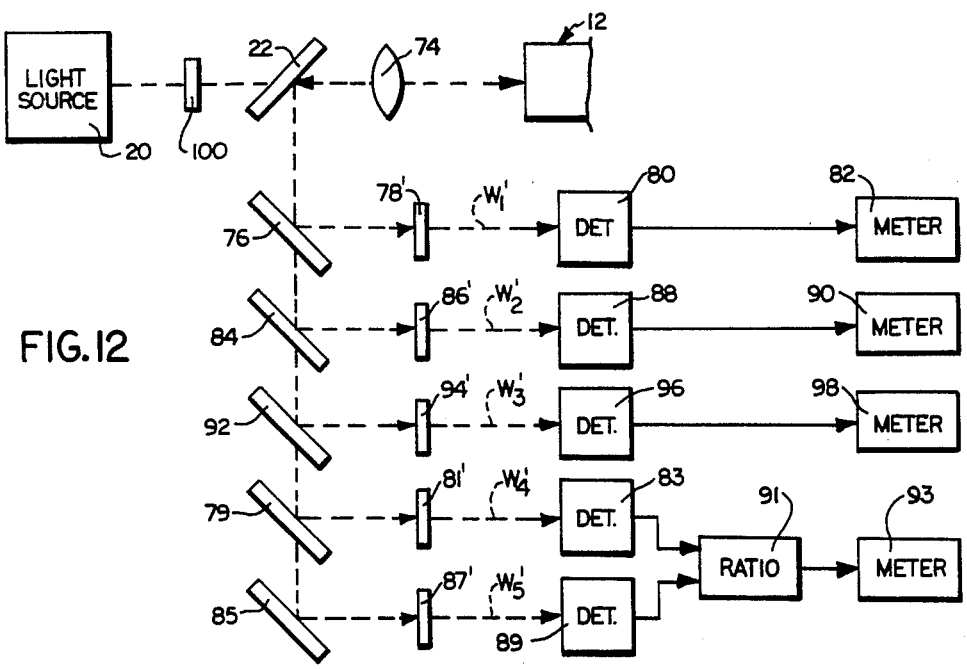
FIG. 12 is a schematic-block diagram illustration of the detector circuitry employed in conjunction with the embodiment of FIGS. 8 and 9.
Figure 13:
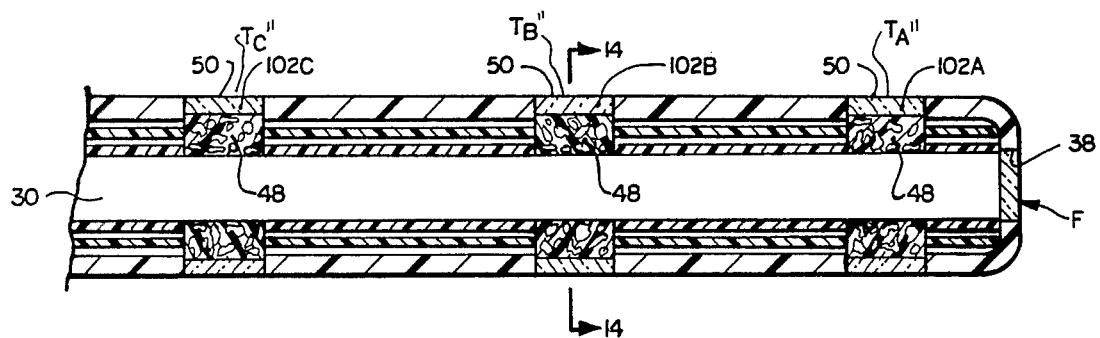
FIG. 13 is an enlarged sectional view of the distal end of the catheter showing a third embodiment of the invention.
Figure 14:
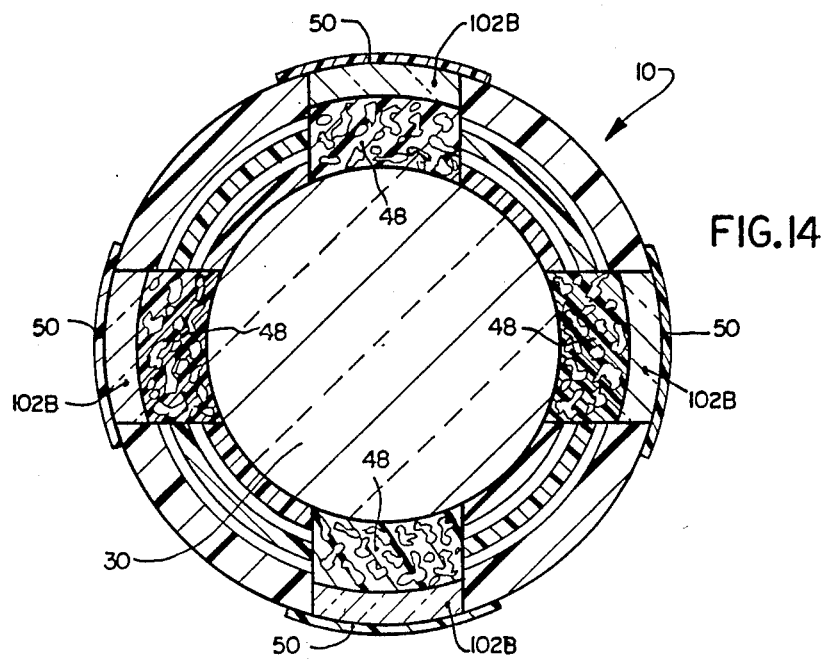
FIG. 14 is a cross sectional view taken along line 14—14 looking in the direction of the arrows in FIG. 13.

Reference is also made to FIGS. 10, 11 and 12. In this embodiment, light transmitted into the optical fiber 12 includes light at wavelengths capable of exciting the fluorescent doped inserts 48A', 48B' and 48C', but none of this excitation light is at any of the wavelengths at which these inserts fluoresce. For this reason, a filter 100 is employed for blocking light in the emission waveband of from approximately 350 to 700 nanometers. This filtered light is then passed by the beam splitter 22 and focused by lens 74 into the proximal end of the optical fiber 12. Within the catheter, the excitation light will be transmitted by core 30. This excitation light is at the excitation wavelengths from 300–350 nanometers and does not include light at a wavelength corresponding to that at which the fluorescent doped transducers fluoresce. In the example given, the excitation wavelengths may be considered a waveband which includes wavelengths from 300–350 nanometers, as is illustrated in FIGS. 10A, 10B and 10C. The transducer inserts will fluoresce at higher wavelengths with that of transducer insert 48C' having an emission wavelength of $W_1'$ on the order of 400 nanometers. The insert 48B' will have an emission wavelength $W_2'$ which will be on the order of 500 nanometers, and transducer 48A' will have an emission wavelength $W_3'$ on the order of 600 nanometers.

Thus, light passing through the optical fiber 10 within the core 30 will be refracted by the transducers 48A', 48B' and 48C' in accordance with the pressure exerted at each transducer. The greater the applied pressure, the greater will be the refraction of light. Consequently, the greater the pressure, then, the greater will be the amplitude or amount of energy emission at wavelengths $W_1'$, $W_2'$ and $W_3'$. Light exiting from the proximal end of the optical fiber 12 will contain light at each of these wavelengths $W_1'$, $W_2'$ and $W_3'$. This light is reflected in part by the beam splitter 22 (FIG. 12) and directed downwardly to the beam splitter 76. A portion of the light striking beam splitter 76 is reflected through a filter 78' which passes only light centered at the wavelength $W_1'$ indicative of the amount of pressure in transducer $T_C'$. This is detected by detector 80 and an electrical signal representative of the pressure level in tranducer $T_C'$ is then displayed as with meter 82. Similarly, a portion of tne light passed through the beam splitter 76 to a beam splitter 84 which reflects a portion of the light to a filter 86' which passes only light centered about the wavelength $W_2'$. This is indicative of the amount of pressure at transducer $T_B'$ and this is converted into an electrical signal by detector 88 with the pressure reading then being displayed as with meter 90.

Also, a portion of the light is passed through a beam splitter 84 and is reflected by beam splitter 92 to a filter 94' which passes only light centered about wavelength $W_3'$. This is indicative of the amount of pressure at transducer $T_A'$ and this is converted into an electrical signal by detector 96 and the electrical output is supplied to meter 98 for providing a visual readout. This excitation light is diminished somewhat in intensity at each transducer in accordance with pressure. Thus, a more accurate reading could be obtained by scaling up each successive reading by an amount related to the other readings.

The light from the light source 20 in FIG. 12 includes light in the red and infrared light regions, i.e., from at least 800 nanometers through 950 nanometers. This longer wavelength light passes through the filter F at the distal end of the catheter and is reflected by blood back into the catheter. As previously discussed, two peak wavelengths are of importance, namely, 805 nanometers and 930 nanometers. The first may be considered as wavelength $W_4'$ and the second as wavelength $W_5'$.

Referring now to FIG. 12, light exiting from the proximal end of the optical fiber 12 is reflected by splitter 22 and a portion of the light passes through beam splitter 76, 84 and 92. Light passing through beam splitter 92 strikes another beam splitter 79 and a portion of the light is directed to a filter 81'. This filter is selected to pass only light at wavelength $W_4'$ and this is passed to a detector 83 which converts the optical intelligence into an electrical signal having a magnitude representative of the magnitude of light at wavelength $W_4'$. This electrical signal is applied as one input to a ratio circuit 91.

In a similar fashion, light passing through splitter 79 strikes a mirror 85 and the reflected light is directed to a filter 87'. This filter passes only light at wavelength $W_5'$ and this is passed to a detector 89 that converts the optical intelligence into an electrical signal having a magnitude representative of the amount of light at this wavelength. This electrical signal is supplied as a second input to the ratio circuit 91. This ratio circuit provides an output signal corresponding to the ratio of light intensity at wavelength $W_4'$ to that at $W_5'$ and this is supplied to a meter 93 for providing a suitable output indication and which, in turn, provides an indication of the percentage of oxygen saturation of the blood.

Reference is now made to FIGS. 13–16 which illustrate a third embodiment of the invention. This embodiment is similar to that described hereinbefore and like components will be identified with like character references and only the differences between this embodiment and the previously described embodiments will be described below in detail.

Figure 8:
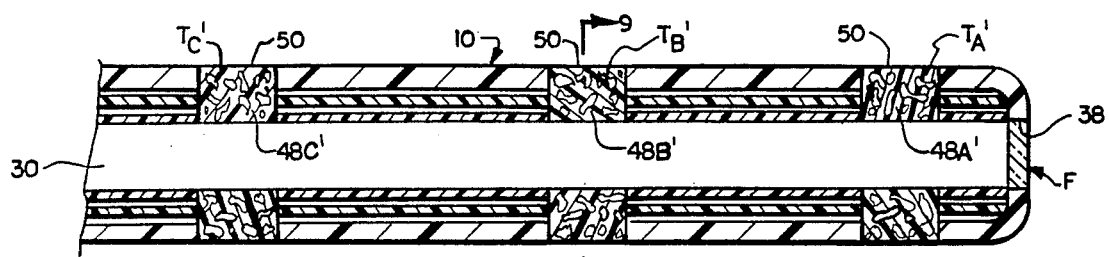
FIG. 8 is an enlarged sectional view of the distal end of the catheter showing a second embodiment of the invention.
Figure 9:
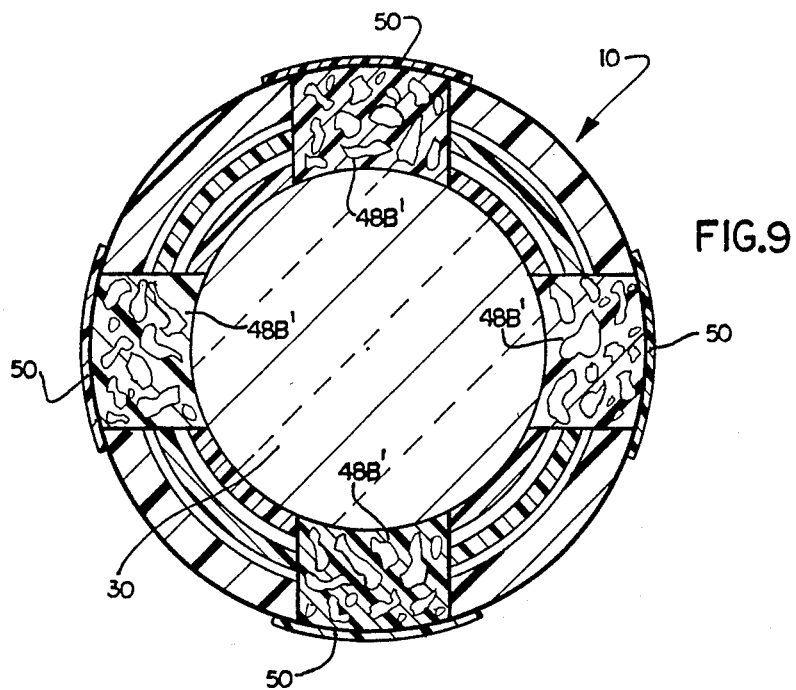
FIG. 9 is an enlarged cross sectional view taken along line 9—9 looking in the direction of the arrows in FIG. 8.

In this embodiment, as in the embodiment shown in FIGS. 8 and 9, the inserts 48 are mounted directly onto the uncladded surface areas of core 30. However, these inserts are not doped as in the case of inserts 48A', 48B' and 48C' of FIGS. 8 and 9. In this embodiment, a flexible, filter coating is applied to the exterior surface of each transducer insert. These filters are illustrated in the drawings as filters 102A, 102B and 102C applied respectively to the exterior surfaces of the transducer inserts 48. The filters, in turn, are each covered by means of a membrane 50, as in the other embodiments. The filters are sufficiently thin and flexible to transmit pressure to the inserts.

Figure 15C:
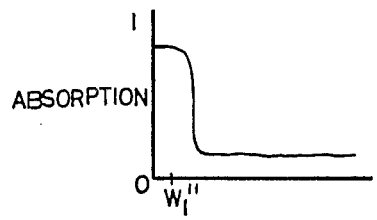
FIGS. 15A-15C are waveforms showing light absorption with respect to wavelength which is useful in describing the embodiment of FIGS. 13 and 14.
Figure 15B:
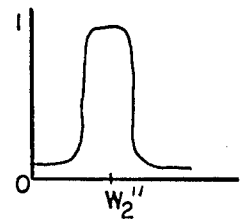
Figure 15A:
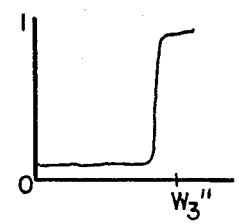

In this embodiment, the transducers are constructed from a nonabsorbent clear sponge-like material exhibiting an index of refraction greater than that of the cladding 32. Thus, the sponge-like material is transparent to light at all wavelengths. The surrounding filters, however, serve to absorb light of a particular wavelength and reflect all other wavelengths. For example, light passing through insert 48 at wavelength $W_1''$ will be refracted by filter 102c and absorbed. Light outside of this waveband will be reflected by the filter and/or by the surrounding cladding 50 and passed back through the insert into core 30. Similarly, at transducer $T_B''$, light which has been passed by the clear transducer insert 48 will be passed to the filter 102B which will, in turn, pass or absorb only light at wavelength $W_2''$ with the remaining light being reflected back into the core. Also, at transducer $T_A''$, light passing through the transducer insert 48 at wavelength $W_3''$ will be, in turn, passed by the filter 102a with the remaining light being reflected back into the core 30. This is indicated by the waveforms of FIGS. 15A–15C. White light supplied by source 20 (FIG. 16) is passed by a beam splitter 22 and focused by a lens 74 into the proximal end of the optical fiber 12. The returning light includes information respecting the pressures at the three transducers in the sense of changes in the amount of light received at wavelengths $W_1''$, $W_2''$ and $W_3''$ from that which was originally introduced at those wavelengths into the optical fiber. For example, the returning light includes light at wavelength $W_1''$. Consequently, the returning light is reflected by beam splitters 22 and 76 and applied to a filter 78'' which passes only light at wavelength $W_1''$. This is detected by detector 80 and converted into an electrical signal which is supplied as one input into a ratio circuit 120.

Light which is reflected from the splitter 22 in an upward direction is supplied to a second beam splitter 122 which reflects a portion of that light through a filter 124. This filter serves to pass light only at wavelength $W_1''$ to a detector 126 which provides an electrical signal to a second input of the ratio circuit 120. The ratio circuit, then, compares the amplitude of light at wavelength $W_1''$ as it enters the optical fiber 12 with that which returns from the optical fiber to obtain a ratio signal. This ratio signal, identified as $V_1$, is then supplied to a suitable meter, such as meter 82, calibrated to provide an output pressure indication at transducer $T_A$ as a function of the difference signal $V_1$. It is to be understood that FIG. 7 could be depicted similarly to improve the signal.

In a similar manner, the light returning from the optical fiber at wavelength $W_2''$ is detected and supplied to a second ratio circuit 130. In this case, the light which passes through splitter 122 is partially reflected from another splitter 132 and is supplied to a filter 134 which passes light only at wavelength $W_2''$, and this is detected by a detector 136. Detector 136 operates to provide an electrical signal to the second input of the ratio circuit 130 representative of the intensity of light at wavelength $W_2''$ as it originally entered the optical fiber 12. The ratio is determined by the ratio circuit 130 as output signal $V_2$ and this is supplied to meter 90 which is calibrated to provide an output indicative of the pressure at transducer $T_B''$ as a function of signal $V_2$.

Also, light returning from the optical fiber 12 at wavelength $W_3''$ is passed by the filter 94'' and detected by detector 96 and the electrical output signal therefrom is supplied to another ratio circuit 140. Light passing through the beam splitter 132 is reflected from a mirror 142 and passed to a filter 144 which passes only light at wavelength $W_3''$. This is detected by detector 146 which supplies an electrical output signal to a second input of the ratio circuit 140. The ratio circuit 140, in turn, provides a ratio output signal $V_3$ which is supplied to a meter 98 calibrated to provide a pressure reading as a function of ratio signal $V_3$.

The light from the light source 20 in FIG. 7 includes light in the red and infrared light regions, i.e., from at least 800 nanometers through 950 nanometers. This longer wavelength light passes through the filter F at the distal end of the catheter and is reflected by blood back into the catheter. As previously discussed, two peak wavelengths are of importance, namely, 805 nanometers and 930 nanometers. The first may be considered as wavelength $W_4''$ and the second as wavelength $W_5''$.

Figure 16:
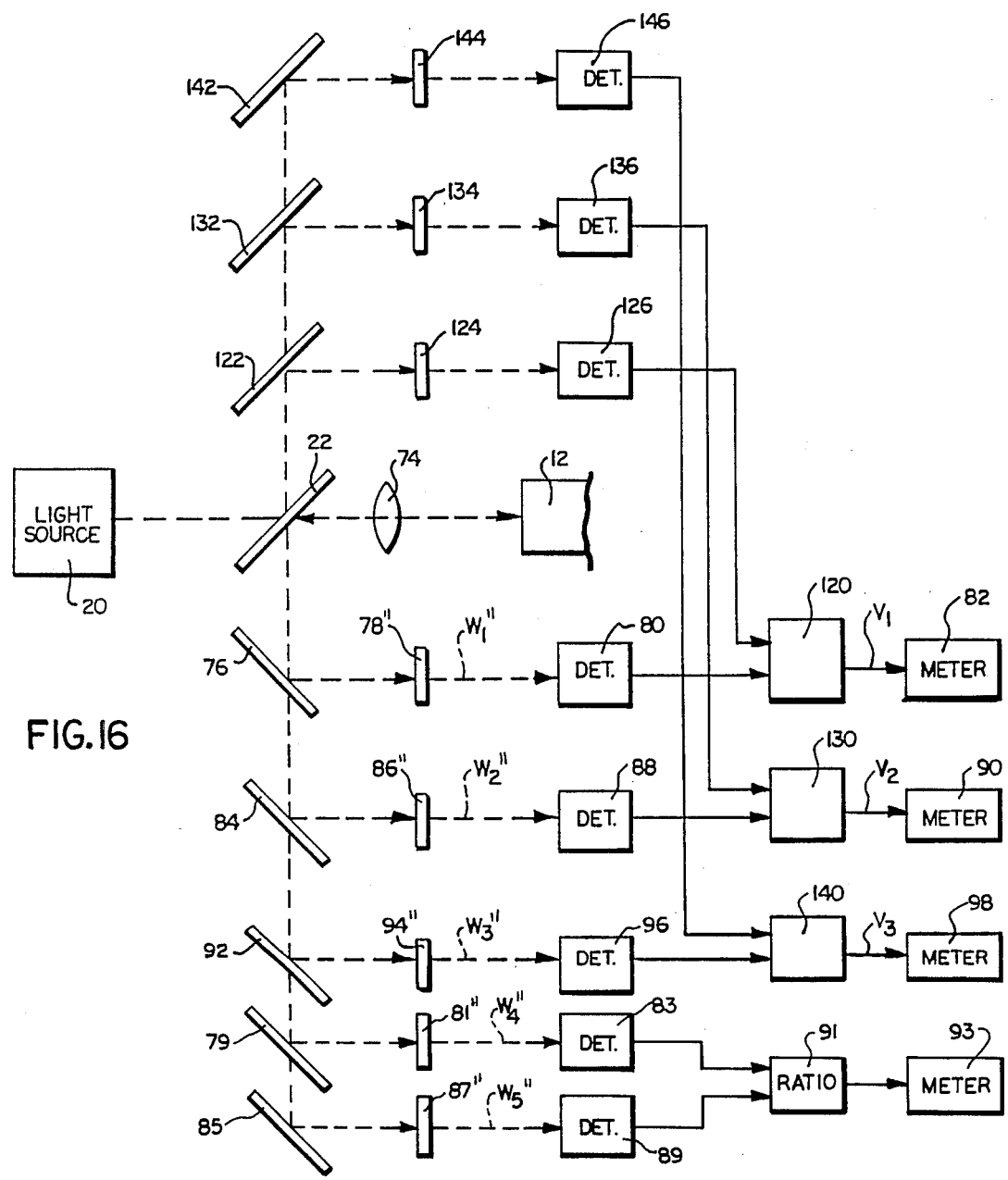
FIG. 16 is a schematic-block diagram illustration of the detector circuitry employed in conjunction with the embodiment of FIGS. 13 and 14.

Referring now to FIG. 16, light exiting from the proximal end of the optical fiber 12 is reflected by splitter 22 and a portion of the light passes through beam splitters 76, 84 and 92. Light passing through beam splitter 92 strikes another beam splitter 79 and a portion of the light is directed to a filter 81''. This filter is selected to pass only light at wavelength $W_4''$ and this is passed to a detector 83 which converts the optical intelligence into an electrical signal having a magnitude representative of the magnitude of light at wavelength $W_4''$. This electrical signal is applied as one input to a ratio circuit 91. In a similar fashion, light passing through splitter 79 strikes a mirror 85 and the reflected light is directed to a filter 87''. This filter passes only light at wavelength $W_5''$ and this is passed to a detector 89 that converts the optical intelligence into an electrical signal having a magnitude representative of the amount of light at this wavelength. This electrical signal is supplied as a second input to the ratio circuit 91. This ratio circuit provides an output signal corresponding to the ratio of light intensity at wavelength $W_4''$ to that at $W_5''$ and this is supplied to a meter 93 for providing a suitable output indication and which, in turn, provides an indication of the percentage of oxygen saturation of the blood.

Although the invention has been described in conjunction with preferred embodiments, it is to be appreciated that various modifications may be made without departing from the spirit and scope of the invention as defined by the appended claims.

Having described specific preferred embodiments of the invention, the following is claimed:

1. Apparatus for use in measuring the degree of oxygen saturation in blood while simultaneously measuring blood pressure and comprising:

an elongated tubular catheter having a proximal end and a distal end with the latter being adapted to be inserted into a blood vessel within a body;

an elongated optical fiber member carried within said catheter and extending throughout the length thereof, said optical fiber member having a light transmitting core coaxially surrounded by cladding means essentially throughout its length, said core being uncladded for at least a portion of its length proximate to the distal end thereof;

filter means located at the distal end of said catheter and positioned forwardly of the distal end of said optical fiber member to receive light therefrom, said filter means being transmissive to light greater than that of a wavelength W, in the red and infrared wavelength region, and reflecting light at wavelengths less than wavelength W so that light of longer wavelengths may be transmitted through said filter means into blood containing both oxygenated and unoxygenated blood and be reflected therefrom back into the distal end of said catheter; and said catheter having at least one side port located adjacent the distal end thereof while proximal of said filter means and in registry with a said uncladded portion of said core, pressure transducer means located in said side port including a flexible transducer member having a pitted surface facing said uncladded core portion and making surface area contact therewith such that the contacting surface area varies with pressure applied to said transducer member acting transversely thereof, said transducer member being constructed of material exhibiting a greater index of refraction than said cladding means so that the intensity of light passing through said core proximate to said transducer means is modulated in its intensity as a function of said pressure.

2. Apparatus as set forth in claim 1 wherein said filter means transmits light having a wavelength on the order of at least 800 nanometers to approximatey 950 nanometers.

3. Apparatus as set forth in claim 1 including means for supplying light into the proximal end of said optical fiber member with said light being over a broad band including that beyond wavelength W and in the red and infrared wavelength region, and detecting means for receiving light exiting from said proximal end, said detecting means including means for detecting the amount of light exiting at wavelengths $W_A$ and $W_B$, both greater than wavelength W, and providing an output indication in dependence thereon representative of the degree of oxygen saturation in the blood.

4. Apparatus as set forth in claim 3 wherein said detecting means includes means for determining the ratio of the amount of light exiting at wavelength $W_A$ to that at wavelength $W_B$.

5. Apparatus as set forth in claim 4 wherein wavelength $W_A$ is on the order of 805 nanometers and wherein wavelength $W_B$ is on the order of 930 nanometers.

6. Apparatus as set forth in claim 3 wherein said pressure transducer means includes light wavelength dependent means for modulating the intensity of light passing through said core proximate to said transducer means at a particular wavelength as a function of said pressure.

7. Apparatus as set forth in claim 6 wherein said catheter means includes a plurality of said side ports longitudinally spaced along its length adjacent the distal end thereof and wherein each of said side ports carries a said pressure transducer means for simultaneously measuring blood pressure at different sites within the said blood vessel whereby said apparatus serves to simultaneously measure blood pressure at multiple sites, while also measuring the degree of oxygen saturation in the blood, each said transducer means includes light wavelength dependent means for modulating light at a particular wavelength different from that at said other transducer means.

8. Apparatus as set forth in claim 7 wherein each said transducer means includes a transducer filter means or passing light within one wavelength range less than wavelength W while reflect light of other wavelengths.

9. Apparatus as set forth in claim 8 wherein said transducer filter means is interposed between a said uncladded core portion and a said transducer member so that only light passed by said transducer filter means is modulated by said transducer member as a function of said pressure.

10. Apparatus as set forth in claim 9 wherein each said transducer filter means exhibits a different index of refraction with each being greater than that of the index of refraction of said cladding means and wherein each said transducer member exhibits an index of refraction greater than that of the associated said transducer filter means.

11. Apparatus as set forth in claim 10 wherein said detecting means includes means for detecting the amount of light in each of said wavelengths below said wavelength W for simultaneously providing a corresponding plurality of output indications representing the pressure acting on each of said transducer members.

12. Apparatus as set forth in claim 8 wherein each said transducer member has an outer surface and each said transducer filter means is located adjacent the outer surface of a said transducer member with each transducer member being constructed of optically transparent material so that light from a said uncladded core portion passes into said transducer member and only light within a given wavelength range is absorbed by said transducer filter means.

13. Apparatus as set forth in claim 12 wherein said detecting means includes means for detecting the difference in the intensity of light transmitted into and received from said proximal end at each of said wavelengths below said wavelength W and simultaneously providing output indications of the pressure acting on each of said transducer members as a function of said detected differences.

14. Apparatus as set forth in claim 7 wherein each said transducer member is doped with a fluorescent dye, said transducer members at the different transducer menas being doped with different fluorescent dyes so that when excited by light each will fluoresce and emit light at a different wavelength such that the emission level at a given wavelength associated with a specific transducer means varies in dependence upon pressure applied to that transducer means.

15. Apparatus as set forth in claim 14 wherein means for supplying light into the proximal end of said optical fiber member includes means for supplying light within a waveband including wavelengths different than that of the emission wavelengths of each of said transducer means, and said detecting means including means for detecting the amount of light at each of said emission wavelengths for simultaneously providing output indications of the pressure acting on each of said transducer means.

* * * * *